United States Patent [19]
Galbo et al.

[11] Patent Number: 6,166,212
[45] Date of Patent: Dec. 26, 2000

[54] PROCESS FOR THE SYNTHESIS OF N-(HYDROXYALKOXY) SUBSTITUTED HINDERED AMINE STABILIZERS

[75] Inventors: James P. Galbo, Wingdale; Robert E. Detlefsen, Putnam Valley, both of N.Y.; Michael P. DiFazio, Mobile; Henry C. Grace, Satsuma, both of Ala.; Christopher Kuell, Danbury, Conn.

[73] Assignee: Ciba Specialty Chemicals Corporation, Tarrytown, N.Y.

[21] Appl. No.: 09/315,704

[22] Filed: May 20, 1999

[51] Int. Cl.⁷ .................................................. C07D 211/40
[52] U.S. Cl. ............................................. 546/216; 546/236
[58] Field of Search ...................... 546/216, 236

[56] References Cited

U.S. PATENT DOCUMENTS

| | | | |
|---|---|---|---|
| 4,691,015 | 9/1987 | Behrens et al. | 544/198 |
| 4,921,962 | 5/1990 | Galbo et al. | 546/184 |
| 5,204,473 | 4/1993 | Winter et al. | 546/188 |
| 5,374,729 | 12/1994 | Galbo | 546/242 |

OTHER PUBLICATIONS

Jahn, U. "Highly efficient generation of radicals . . . " J. Org. chem. v.63(21) 7130–31, 1998.
Rozantsev et al., Synthesis, (1971), pp. 190–202.
Asmus et al., Int. J. Radiat. Biol., (1976), vol. 29, No. 3, pp. 211–219.
Nigam et al., JCS, Trans. Faraday Soc., (1976), vol. 72, pp. 2324–2340.
Barton et al., Tetrahedron, (1996), vol. 52, 10301.

*Primary Examiner*—Ceila Chang
*Attorney, Agent, or Firm*—Luther A. R. Hall

[57] ABSTRACT

N-(Hydroxyalkoxy) hindered amine stabilizers are prepared by reacting the corresponding N-oxyl compound with a peroxide or organic hydroperoxide and a catalytic amount of a metal salt or metal-ligand complex in an alcohol solvent. These N-(hydroxyalkoxy) hindered amines are particularly useful as stabilizers for polyolefins, thermoplastic polyolefins and automotive coating compositions.

40 Claims, No Drawings

PROCESS FOR THE SYNTHESIS OF N-(HYDROXYALKOXY) SUBSTITUTED HINDERED AMINE STABILIZERS

The instant invention pertains to a process for preparing N-(hydroxyalkoxy) substituted hindered amine compounds by the reaction of the corresponding N-oxyl intermediate with a peroxide or organic hydroperoxide and a catalytic amount of a metal salt or metal-ligand complex in an alcohol solvent.

BACKGROUND OF THE INVENTION

The compounds made by the instant process, because they are less basic than normal unsubstituted or N-alkyl substituted hindered amines, are particularly effective in the stabilization of polymer compositions where the activity of the more basic hindered amines is significantly reduced by interaction with the polymer substrate or additives in the polymer system. Examples of polyolefin compositions in which the instant compounds are particularly effective include thermoplastic polyolefins where pigment interactions with basic hindered amine stabilizers interfere with painting the substrate, in greenhouse films and agricultural where acidic residues from pesticides interfere with the activity of normal hindered amine stabilizers, and in flame retardant polyolefins where acidic residues from the decomposition of halogenated flame retardants deactivate normal more basic hindered amine stabilizers. Examples of automotive coatings compositions in which the instant compounds are effective include thermoset acrylic resins with melamine crosslinking agents as well as acrylic alkyd or polyester resins with isocyanate crosslinking agents and epoxy resins with carboxylic acid, anhydride or amine crosslinking agents.

The instant N-(hydroxyalkoxy) (NOROL) compounds are described in copending application Ser. No. 09/257,711.

U.S. Pat. No. 4,921,962 describes a process for the formation of N-hydrocarbyloxy derivatives of sterically hindered amines in which a hindered amine or N-oxyl substituted hindered amine is reacted with a hydrocarbon solvent in the presence of a hydroperoxide and a metal carbonyl, metal oxide or metal alkoxide catalyst. The instant process describes the synthesis of hindered amine compounds exclusively from alcohols whereas U.S. Pat. No. 4,921,962 is solely restricted to the use of hydrocarbon solvents. The process of U.S. Pat. No. 4,921,962 minimizes the amount of water left in the reaction mixture as a result of using commercially available aqueous hydroperoxide solutions. This is accomplished by azeotropic distillation with the hydrocarbon solvent, extraction of an aqueous hydroperoxide with hydrocarbon solvent or the use of a hydroperoxide with very low water content such as 90% tert-butyl hydroperoxide with contains only 5% water. The instant process does not teach the removal of water from the aqueous hydrogen peroxide or organic hydroperoxide used in the instant process. Water can even be used as a cosolvent in the instant process. Furthermore, the prior art process described in U.S. Pat. No. 4,921,962 specifically teaches the use of tertiary alkyl peroxides whereas hydrogen peroxide is the most preferred peroxide in the instant process. The preferred metal catalysts for the prior art process described in U.S. Pat. No. 4,921,962 are chromium trioxide and molybdenum catalysts whereas the preferred metal catalysts in the instant process are iron(II), iron(II), copper(I) and copper(II) salts or metal-ligand complexes.

U.S. Pat. No 5,374,729 describes a process for the preparation of N-methoxy derivatives of hindered amines from the reaction of the corresponding N-oxyl compound with methyl radicals produced by the combination of aqueous hydrogen peroxide and a peroxide-decomposing transition metal salt in the presence of dimethyl sulfoxide. The instant process involves the formation of alcohol substituted derivatives of the hindered amines.

4-Hydroxy-1-oxyl-2,2,6,6-tetramethylpiperidine and 4-oxo-1-oxyl-2,2,6,6-tetra-methylpiperidine have been used to trap carbon centered radicals formed from methanol, ethanol, 2-propanol and 2-methyl-2-propanol as reported by S. Nigam et al., J. Chem. Soc., Trans. Faraday Soc., 11976, (72), 2324 and by K.-D. Asmus et al., Int. J. Radiant. Biol., 1976, (29), 211. The carbon centered radical were produced by reaction of the specified alcohols with hydroxy radicals formed by the reaction of hydrated high energy electrons with nitrous oxide. The instant process is clearly distinct from these prior art disclosures.

D. H. R. Barton et al., Tetrahedron, 1996, (52), 10301 describe the formation of N-alkoxy-2,2,6,6-tetramethylpiperidine derivatives in the reaction of unactivated hydro-carbons with iron(II) and iron(III) species, hydrogen peroxide and various coadditives in the presence of N-oxyl-2,2,6,6-tetramethylpiperidine (TEMPO) even though some of the hydrocarbon solvent is oxidized to the corresponding alcohol in the reaction. Again, this article does not disclose or suggest the instant process.

The instant process provides a convenient method for the synthesis of a novel class of hindered amine stabilizer compounds as disclosed in copending application Ser. No. 09/257,711. These compounds, because of the presence of a polar alcohol functionality on the N-atom of the hindered amine ring, complement the relatively non-polar N-O-hydrocarbon hindered amine derivatives described in U.S. Pat. No. 5,204,473. The polar hydroxy group and the N-alkoxy moiety which reduces hindered amine basicity are introduced into the hindered amine moiety in one simple reaction.

The instant process also takes advantage of the compatibility of many alcohols with commercially available aqueous hydrogen peroxide and organic hydroperoxide solutions. The process also uses only catalytic quantities of a metal salt and does not require high temperatures.

DETAILED DISCLOSURE

The process for the synthesis of the N-(hydroxyalkoxy) substituted hindered amines of formula I

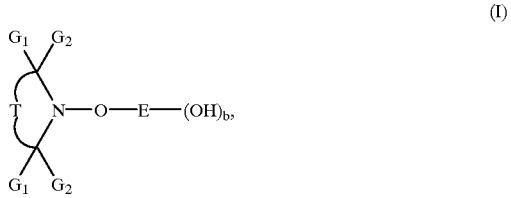

wherein
  $G_1$ and $G_2$ are independently alkyl of 1 to 4 carbon atoms, or $G_1$ and $G_2$ together are pentamethylene;
  T is a divalent organic radical required to complete a five- or six-membered ring containing the hindered amine nitrogen atom and two quaternary carbon atoms substituted by $G_1$ and $G_2$;
  E is a (b+1) valent alkylene radical of 2 to 18 carbon atoms, an alkenylene radical of 3 to 19 carbon atoms, a cycloalkylene radical of 5 to 12 carbon atoms, a cycloalkenylene radical of 5 to 12 carbon atoms or an alkylene radical of 2 to 4 carbon atoms substituted by phenyl or by phenyl substituted by one or two alkyl of 1 to 4 carbon atoms; and b is 1, 2 or 3; with the proviso that b cannot exceed the number of saturated carbon atoms in E, and when b is 2 or 3, each hydroxyl group is bonded to a different carbon atom in E;

which process comprises reacting a N-oxyl hindered amine of formula II

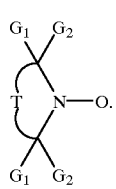

(II)

with an alcohol of formula III

(III)

in the presence of a peroxide or organic hydroperoxide and a catalytic amount of a metal salt or metal-ligand complex.

The N-oxyl compounds of formula II may be prepared by the reaction of the corresponding N-H hindered amine with hydrogen peroxide and sodium tungstate as described by E. G. Rozantsev et al., in Synthesis, 1971, 190; or with tert-butyl hydroperoxide and molybdenum (VI) as taught in U.S. Pat. No. 4,691,015.

More specifically, the instant process involves the reaction of a mixture of 5 to 100 moles of the alcohol of formula III, 1 to 15 moles of hydrogen peroxide or organic hydroperoxide, and 0.001 to 0.5 moles of metal salt or metal-ligand complex per mole of N-oxyl compound of formula II. The reaction is carried out at a temperature in the range of 20° to 100° C.

The alcohol serves two functions both as reactant and as solvent for the reaction. A mixture of products may result if the alcohol contains non-equivalent carbon-hydrogen bonds which are reactive in the instant process. For example, tert-butyl alcohol can give only one product whereas tert-amyl alcohol can give three distinct reaction products. A cosolvent may be used if the alcohol is a solid at the temperature of the reaction or if the metal salt or metal-ligand complex is not very soluble in the alcohol. Typical cosolvents are water, methanol and ethylene glycol.

The instant process uses a less than stoichiometric amount, based on peroxide, of a transition metal salt or a metal-ligand complex with the metal chosen from groups IVA, VA, VIIA, VIIIA or IB of the periodic table. Iron(II), iron(III), copper(I) and copper(II) are the most effective catalysts. The metal may be in the form of a simple salt such as a metal chloride or sulfate, a metal salt of an organic acid such as acetic acid, or a metal oxide which may also contain a cation from group IA or IIA of the periodic table, such as sodium metavanadate. The metal may also be complexed with a ligand such as 2,2'-dipyridyl, ethylenediaminetetraacetic acid or its disodium salt, triphenylphosphine oxide, or the anion of acetylacetone. These metal ligand complexes are items of commerce or may be formed in situ by mixing a metal salt with the ligand. The amount of ligand may be less than the amount required to completely complex the metal based on its oxidation state. The metal salt or metal-ligand complex may be bound to a solid support such as silica gel so that it can be recovered and reused.

A mineral acid or sulfonic acid may be added to the reaction mixture in an amount corresponding to up to one mole per mole of nitroxyl moiety.

The instant process can be run in air or in an inert atmosphere such a nitrogen or argon.

There are several variations of the instant process. One variation involves the addition of a solution of aqueous hydrogen peroxide or organic hydroperoxide to a mixture of the N-oxyl hindered amine, the alcohol and cosolvent (if used) and acid (if used), and metal salt or metal-ligand complex which has been brought to the desired temperature for reaction. The proper temperature is maintained by controlling the rate of peroxide addition and/or by using a heating or cooling bath. After the peroxide is added, the reaction mixture is stirred till the starting N-oxyl compound of formula II has disappeared or is no longer being converted to the compound of formula I. The reaction is best monitored by thin layer chromatography, gas chromatography or liquid chromatography. Additional portions of metal salt or metal-ligand complex can be added while the reaction is in progress. After the initial peroxide charge has been added to the reaction mixture, more peroxide can be added dropwise to bring the reaction to completion.

A second variation of the instant process is to simultaneously add separate solutions of the peroxide and the nitroxyl compound to a mixture of the alcohol, cosolvent (if used), acid (if used) and metal salt or metal-ligand complex. The nitroxyl compound may be dissolved in water or the alcohol solvent used in the reaction. Some of the nitroxyl compound may be introduced into the reaction mixture prior to starting the peroxide addition, and all of the nitroxyl compound should be added prior to completing the peroxide addition.

Another variation of the instant process involves the simultaneous addition of separate solutions of the peroxide and of the aqueous or alcohol solution of the metal salt or metal-ligand complex to a mixture of the nitroxyl compound, alcohol, cosolvent (if used), and acid (if used). Some of the metal may be introduced into the reaction mixture prior to starting the peroxide addition.

Still another variation of the instant process is the simultaneous addition of separate solutions of the peroxide, of the aqueous or alcohol solution of the nitroxyl compound, and of an aqueous or alcohol solution of the metal salt or metal-ligand complex to the alcohol, cosolvent (if used) and acid (if used). A portion of the nitroxyl compound and/or metal salt or metal-ligand complex may be introduced into the reaction mixture prior to starting the peroxide addition. All of the nitroxyl compound should be added prior to completing the peroxide addition.

If acid is used in the reaction, the acid may be added in one portion at the beginning of the reaction, or a portion of acid may be added at the beginning of the reaction and the remainder added while the reaction is in progress; or all of the acid may be added while the reaction is in progress. Some or all of the acid may be mixed with the metal salt if the metal salt is added as a solution while the reaction is in progress.

If a metal-ligand complex is prepared in situ, the metal salt and ligand are most effectively mixed prior to contact with the nitroxyl compound.

At the end of the reaction, the residual peroxide should be carefully decomposed prior to the isolation of any products.

PREFERRED EMBODIMENTS $G_1$ and $G_2$ are preferably methyl.

T is preferably 2-hydroxy-1,3-propanediyl or 2-oxo-1,3-propanediyl.

When b is 1, —E—(OH) is a carbon centered radical formed preferably from 2-methyl-2-propanol (=tert-butyl alcohol), 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, 2-octanol, cyclohexanol, cyclooctanol, allyl alcohol, phenethyl alcohol or 1-phenyl-1ethanol; and—E—(OH) is most preferably formed from 2-methyl-2-propanol (=tert-butyl alcohol) or cyclohexanol.

When b is 2, —E—(OH)$_2$ is a carbon centered radical formed preferably from 1,2-propanediol, 1,3-propanediol, 1,2-butanediol, 1,4-butanediol, 2,2-dimethyl-1,3-propanediol, 2,5-dimethyl-2,5-hexanediol, 1,2-cyclohexanediol, 1,3-cyclohexanediol or 1,4-cyclohexanediol; and —E—(OH)$_2$ is formed most preferably from 1,4-butanediol, 2,2-dimethyl-1,3-propanediol, 1,2-cyclohexanediol, 1,3-cyclohexanediol or 1,4-cyclo-hexanediol.

When b is 3, —E—(OH)$_3$ is a carbon centered radical formed preferably from 1,1,1-tris(hydroxymethyl)ethane, 2-ethyl-2-(hydroxymethyl)-1,3-propanediol, 1,2,4-butanetriol or 1,2,6-hexanetriol; and —E—(OH)$_3$ is formed most preferably from 1,1,1-tris(hydroxymethyl)ethane or 2-ethyl-2-(hydroxymethyl)-1,3-propanediol.

b is preferably 1 or 2; most preferably 1.

Preferably the peroxides are hydrogen peroxide, the addition compound of urea and hydrogen peroxide, tert-butyl hydroperoxide, tert-amyl hydroperoxide and cumene hydroperoxide. More perferably the peroxides are hydrogen peroxide and the addition compound of urea and hydrogen peroxide; and most perferably hydrogen peroxide.

The hydrogen peroxide may be 15 to 50% by weight solution in water, preferably 30 to 50% by weight solution in water.

Preferably, the metals are chosen from the groups IVA, VA, VIIA, VIIIA and IB of the periodic table. More preferred are iron(II), iron(III), copper(I), copper(II), cobalt(II), cobalt(III), manganese(II), manganese(III), vanadium(II), vanadium(III), cerium(III) and titanium(III). Most preferred are iron(II), iron(III), copper(I) and copper(II).

Preferably the counterions for the above metals are chloride, sulfate, acetylacetonate (acac), acetate, citrate, oxalate, nitrate, perchlorate, cyanide, hydroxide, phosphate, pyrophosphate and oxide.

Preferably the ligands for the above metals are 2,2'dipyridyl, 2,2':6,2"-terpyridyl, 1,10-phenanthroline, ethylenediaminetetraacetic acid, ethylenediaminetetraacetic acid disodium salt, pyridine, picolinic acid, 2-pyrazinecarboxylic acid, aromatic diimines formed from the reaction of aniline or substituted anilines with 1,2-diketones such as 2,3-butanedione, and triphenylphosphine oxide.

Preferably the metal salts are ferrous chloride, ferric chloride, ferric acetyl-acetonate, ferric phosphate, ferric pyrophosphate, ferrous phosphate, ferrous sulfate, ferric sulfate, ferrous acetate, ferric citrate, ferrous oxalate, ferric oxalate, ferric nitrate, ferrous perchlorate, ferric perchlorate, cuprous chloride, cupric chloride, cuprous sulfate, manganous chloride, sodium metavanadate, titanous chloride, vandium(II) chloride and vanadium(III) chloride. Most preferred metal salts are ferrous chloride, ferric chloride, ferric acetylacetonate, ferric phosphate, ferric pyrophosphate, ferrous phosphate, ferrous sulfate, ferric sulfate and cupric sulfate.

Preferably the metal-ligand complexes are those from iron(II), iron(III), copper(I) or copper(II) salts and 2,2'-dipyridyl, triphenylphosphine oxide, ethylenediaminetetraacetic acid or ethylenediaminetetraacetic acid disodium salt. Most preferably, the metal-ligand complex are those from ferrous chloride or ferric chloride and 2,2'-dipyridyl.

Preferably the acids are hydrochloric acid, sulfuric acid, methanesulfonic acid, oxalic acid, trifluoroacetic acid, polyphosphoric acid and phosphoric acid; most preferably, the acid is methanesulfonic acid, polyphosphoric acid and phosphoric acid.

The preferred amount of alcohol solvent for the instant process depends to some extent on the relative number of reactive hydrogens on the alcohol reactant and the hindered amine nitroxyl compound. The reaction is typically carried out with a ratio of 5 to 100 moles of solvent per mole of nitroxyl moiety with the preferred ratio being 10 to 50 moles per mole of nitroxyl moiety, and the most preferred ratio being 10 to 30 moles of solvent per mole of nitroxyl moiety.

The preferred amount of hydrogen or organic hydroperoxide is 1 to 20 moles per mole of nitroxyl moiety, with the more preferred amount being 1 to 5 moles of peroxide per mole of nitroxyl moiety and the most preferred amount being 1 to 3 moles of peroxide per mole of nitroxyl moiety.

The preferred amount of metal salt or metal-ligand complex is 0.001 to 0.5 molar equivalent per mole of nitroxyl moiety, with a ratio of 0.001 to 0.05 moles of metal salt or metal-ligand complex per mole of nitroxyl moiety being the most preferred.

If an acid is used in the instant process, the preferred amount of acid is 0.01 to 1 molar equivalent per mole of nitroxyl moiety, with a ratio of 0.01 to 0.5 molar equivalents of acid per mole of nitroxyl moiety being most preferred.

The reaction is run at 20° to 100° C.; preferably at 60° to 100° C.

The following examples are for illustrative purposes only and are not to be construed to limit the instant invention in any manner whatsoever.

EXAMPLE 1

Reaction of 1-Oxyl-2,2,6,6-tetramethylpiperidin-4-one with Cyclohexanol

A solution of 55 g (0.49 mol) of 30% aqueous hydrogen peroxide is added dropwise over a 4.25 hour period to a mixture of 23.5 g (0.14 mol) of 1-oxyl-2,2,6,6-tetra-methyl-piperidin-4-one and 4.0 g (0.020 mol) of ferrous chloride tetrahydrate in 14 g (0.14 mol) of cyclohexanol and 150 g of cyclohexane. The reaction temperature is maintained at approximately 40° C. throughout the addition. The reaction mixture is stirred at 40° C. for three hours after the peroxide addition is complete. A second portion of 30% aqueous hydrogen peroxide (10 g, 0.09 mol) is added and the reaction mixture is heated at 40° C. for seven hours. After the mixture is cooled to room temperature, sodium sulfite (5 g) is added. The reaction temperature is carefully brought to 60° C. for one hour to decompose excess peroxide. Upon cooling, the organic layer is separated, dried over anhydrous magnesium sulfate, and concentrated to give 22.6 g of a brown oil. The oil is dissolved in cyclohexane and passed through silica gel with cyclohexane and then 1:2 (v/v) ethanol/cyclohexane to afford 16.5 g of a yellow oil.

Analysis by gas chromatography and mass spectrometry shows the product to be a mixture which contains at least four isomers of 1-(hydroxycyclohexyloxy)-2,2,6,6-tetramethylpiperidin-4-one.

EXAMPLE 2

Bis [1-(2-hydroxy-2-methylpropoxy)-2,2,6,6-tetramethylpiperidin-4-yl)] Sebacate

A solution of 73 g (0.64 mol) of 30% aqueous hydrogen peroxide is added dropwise over a 3.5 hour period to a mixture of 30.0 g (0.059 mol) of bis(1-oxyl-2,2,6,6-tetramethylpiperidin-4-yl) sebacate and 4.7 g (0.024 mol) of ferrous chloride tetrahydrate in 150 g of tert-butyl alcohol and 6 g of water. The reaction temperature is kept at approximately 40° C. throughout the peroxide addition. The reaction mixture is stirred at 40° C. for four hours after the addition is complete. The reaction mixture is diluted with 150 g of ethyl acetate. A solution of 100 g of 20% aqueous sodium sulfite solution is added and the reaction mixture is stirred for 1.5 hours at 45–60° C. to decompose excess peroxide. The aqueous layer is extracted with 100 g of ethyl acetate, and the combined organic layers are washed with 200 g of 5% sulfuric acid. Solvent is evaporated to obtain 39.4 g of a pale yellow liquid which is purified by flash chromatography on silica gel with a 4:1:5 part mixture (by volume) of ethyl acetate:isopropanol:hexane to afford 19.1 g (49% yield) of the title compound as a pale yellow oil.

$^1$Hnmr (CDCl$_3$): δ=3.65 ppm (4H, —NOCH$_2$—)

EXAMPLE 3

Reaction of Bis(1-oxyl-2,2,6,6-tetramethylpiperidin-4-yl) Sebacate with Cyclohexanol A solution of 70 g (0.62 mol) of 30% aqueous hydrogen peroxide is added dropwise over 2.75 hours to a mixture of 32.4 g (0.063 mol) of bis(1-oxyl-2,2,6,6-tetramethylpiperidin-yl) sebacate and 5.0 g (0.025 mol) of ferrrous chloride tetrahydrate in 100 g of cyclohexanol. The reaction temperature is maintained at 40–45° C. during the addition. The reaction mixture is then stirred at 40° C. for five hours and during this time, fresh 50% aqueous hydrogen peroxide (5.0 g, 0.074 mol) is added to the reaction mixture in two equal portions. The following day, the reaction mixture is heated to 40° C., another portion of 50% aqueous hydrogen peroxide (2.5 g, 0.037 mol) is added, and the mixture is maintained at 40° C. for another five hours. A solution of 100 g of 20% aqueous sodium sulfite is added to the mixture and the reaction temperature is maintained at 70° C. for 45 minutes to decompose excess hydrogen peroxide. The combined organic layers are concentrated to give 151 g of crude product. Water is added, and residual cyclohexanol is removed by steam distillation. The remaining 50 g of crude product is purified by flash chromatography on silica gel with a 10:1:10 part mixture of ethyl acetate:ethanol:hexane to afford 32.9 g of an oil.

NMR analysis shows that the oil contains bis[1-(trans-2-hydroxycyclohexyloxy)-2,2,6,6-tetramethylpiperidin-4-yl] sebacate in addition to other structural isomers of said sebacate compound.

EXAMPLE 4

Reaction of 4-Hydroxy-1-oxyl-2,2,6,6-tetramethylpiperidine with Cyclohexanol

A solution of 50 g (0.74 mol) of 50% aqueous hydrogen peroxide is added dropwise over a 1.75 hour period to a mixture of 35.0 g (0.20 mol) of 4-hydroxy-1-oxyl-2,2,6,6-tetramethylpiperidine and 10.0 g (0.050 mol) of ferrous chloride tetrahydrate in 100 g of cyclohexanol. The reaction temperature is maintained at approximately 40–45° C. throughout the addition. After the peroxide addition is complete, the reaction mixture is stirred at 40° C. for five hours. The mixture is cooled to room temperature and a solution of 100 g of 20% aqueous sodium sulfite is added. The reaction mixture is carefully heated at 60° C. for one hour to decompose excess peroxide. After acetone is added to the organic layer, the crude product mixture is filtered to remove solids and the filtrate is concentrated. Water is added and residual cyclohexanol is removed by steam distillation. The crude product is purified by flash chromatography on silica gel with 2:1 (v/v) hexane/ethyl acetate to afford 36.3 g of a yellow oil.

Analysis by mass spectrometry shows the oil to be a mixture of isomers of 1-(hydroxycyclohexyloxy)-4-hydroxy-2,2,6,6-tetramethylpiperidine and 1-(dihydroxy-cyclohexyloxy)-4-hydroxy-2,2,6,6-tetramethylpiperidine.

EXAMPLE 5

Reaction of 2,4-Bis[N-(1-oxyl-2,2,6,6-tetramethylpiperidin-4-yl)butylamino]-6-chloro-s-triazine with Cyclohexanol A solution of 30 g (0.44 mol) of 50% aqueous hydrogen peroxide is added over a 2 hour period to a mixture of 39.4 g (0.070 mol) of 2,4-bis[N-(1-oxyl-2,2,6,6-tetramethylpiperidin-4-yl)butylamino]-6-chloro-s-triazine and 7.0 g (0.035 mol) of ferrous chloride tetrahydrate in 150 g of cyclohexanol at a temperature of 40–45° C. The reaction mixture is stirred at 40° C. for ten hours after the peroxide addition is complete, and during this time, another 19 g (0.28 mol) portion of 50% aqeuous hydrogen peroxide is added. Another portion of 50% aqueous hydrogen peroxide (25 g, 0.37 mol) is added while the reaction mixture is heated at 50–65° C. for four hours. The reaction mixture is treated with a solution of 100 g of 20% aqueous sodium sulfite at 60° C. for one hour to decompose residual peroxide. The organic layer is concentrated to a brown oil which is extracted thrice with cyclohexane and once with ethyl acetate. The combined extracts are concentrated to afford 43.4 g of a yellow solid.

EXAMPLE 6

4-Hydroxy-1-(2-hydroxy-2-methylpropoxy)-2,2,6,6-tetramethylpiperidine

A solution of 50.7 g (0.75 mol) of 50% aqueous hydrogen peroxide mixed with 25 mL of tert-butyl alcohol is added over two hours to a mixture of 25.8 g (0.15 mol) of 4-hydroxy-1-oxyl-2,2,6,6-tetramethylpiperidine, 8.95 g (0.045 mol) of ferrous chloride tetrahydrate and 110 mL of tert-butyl alcohol at 50° C. The reaction mixture is then maintained at 50° C. for six hours and monitored by gas chromatography. Another 17.7 g (0.26 mol) of 50% hydrogen peroxide is added and the reaction mixture is heated at 50° C. for two more hours to bring about complete reaction of the starting nitroxyl compound. The reaction mixture is filtered to remove solids, and the filtrate is diluted with water. The tert-butyl alcohol-water solution is extracted three times with methylene chloride and the aqueous layer is thoroughly extracted with ethyl acetate to afford 7.4 g of the title compound. The combined organic layers are washed once with saturated sodium chloride, dried over anhydrous magnesium sulfate and concentrated to give 21.7 g of an orange oil. The orange oil is purified by flash chromatography on silica gel with 3:2 heptane:ethyl acetate to afford another 12.4 g of the title compound and 4.2 g of a compound which has the same retention time by gas chromatography as an authenic sample of 1-(2-hydroxy-2-methylpropoxy)-2,2,6,6-tetramethylpiperidin-4-one.

Examples 6A to 6D illustrate the effect of adding a ligand to the procedure described in Example 6.

EXAMPLE 6A

4-Hydroxy-1-(2-hydroxy-2-methylpropoxy)-2,2,6,6-tetramethylpiperidine

Ferrous chloride tetrahydrate (0.99 g, 5.0 mmol) is added to 400 mL of tert-butyl alcohol which is heated to 40° C. The mixture is stirred for 15 minutes and 0.78 g (5.0 mmol) of 2,2'-dipyridyl is added to the tert-butyl alcohol solution. The solution is then stirred for five minutes and 17.2 g (100 mmol) of 4-hydroxy-1-oxyl-2,2,6,6-tetramethylpiperidine is added. A solution of 49 g (0.72 mol) of 50% aqueous hydrogen peroxide mixed with 100 mL of tert-butyl alcohol is added to the reaction mixture over a 10-hour period at 40–45° C. Another 6 g (0.088 mol) of 50% aqueous hydrogen peroxide is then added while the reaction mixture is heated at 45° C. for four hours until the starting nitroxyl compound is reacted. Analysis by gas chromatography shows the reaction mixture contains 6 area % of 1-(2-hydroxy-2-methylpropoxy)-2,2,6,6-tetramethylpiperidin-4-one compared to 22 area % in Example 6. Solids are removed by filtration, and after 1.5 g of sodium borohydride is added, the filtrate is stirred for one hour. The filtrate is diluted with water, and the mixture is thoroughly extracted with ethyl acetate. The extract is concentrated to afford 24.2 g of a light tan crystalline solid which has the same gas chromatography retention time as an authenic sample of the title compound. In a similar experiment, the final product is recrystallized several times from heptane to obtain 16.9 g (69% yield) of the title compound, melting at 127–131° C.

EXAMPLE 6B

4-Hydroxy-1-(2-hydroxy-2-methylpropoxy)-2,2,6,6-tetramethylpiperidine

A solution of 32.3 g (475 mmol) of 50% aqueous hydrogen peroxide mixed with 35 mL of tert-butyl alcohol is added over six hours at 45–50° C. to a mixture prepared by adding sequentially 0.362 g (1.2 mmol) of ethylenediaminetetraacetic acid, 55 mL of tert-butyl alcohol and 17.2 g (100 mmol) of 4-hydroxy-1-oxyl-2,2,6,6-tetramethylpiperidine to a solution of 0.80 g (4 mmol) of ferrous chloride dissolved in 5 mL of water. Analysis by gas chromatography shows 15% starting nitroxyl compound remains at the end of the peroxide addition. The reaction mixture is stirred for one hour at 45–50° C. and then for 72 hours at 25° C. to complete the reaction. Analysis by gas chromatography shows the reaction mixture contains a ratio of 7 parts of the title compound to 1 part of 1-(2-hydroxy-2-methylpropoxy)-2,2,6,6-tetramethylpiperidin-4-one.

EXAMPLE 6C

4-Hydroxy-1-(2-hydroxy-2-methylpropoxy)-2,2,6,6-tetramethylpiperidine

The procedure of Example 6B is repeated using triphenylphosphine oxide in place of the ethylenediaminetetraacetic acid.

EXAMPLE 6D

4-Hydroxy-1-(2-hydroxy-2-methylpropoxy)-2,2,6,6-tetramethylpiperidine

The procedure of Example 6B is repeated using ethylenediaminetetraacetic acid disodium salt in place of ethylenediaminetetraacetic acid.

EXAMPLE 7

Bis[1-(2-hydroxy-2-methylpropoxy)-2,2,6,6-tetramethylpiperidin-4-yl] Adipate

Aqueous hydrogen peroxide is added to a mixture of bis(1-oxyl-2,2,6,6-tetra-methylpieridin-4-yl) adipate and ferrous chloride tetrahydrate in tert-butyl alcohol at 30–50° C. Excess peroxide is decomposed with aqueous sodium sulfite solution. The organic layer is concentrated and the crude product is purified by flash chromatography on silica gel to afford the title compound.

EXAMPLE 8

Bis[1-(2-hydroxy-2-methylpropoxy)-2,2,6,6-tetramethylpiperidin-4-yl] Glutarate

Aqueous hydrogen peroxide is added to a mixture of bis(1-oxyl-2,2,6,6-tetra-methylpieridin-4-yl) glutarate and ferrous chloride tetrahydrate in tert-butyl alcohol at 30–50° C. Excess peroxide is decomposed with aqueous sodium sulfite solution. The organic layer is concentrated and the crude product is purified by flash chromatography on silica gel to afford the title compound.

EXAMPLE 9

Bis[1-(2-hydroxy-2-methylpropoxy)-2,2,6,6-tetramethylpiperidin-4-yl] Succinate

Aqueous hydrogen peroxide is added to a mixture of bis(1-oxyl-2,2,6,6-tetra-methylpieridin-4-yl) succinate and ferrous chloride tetrahydrate in tert-butyl alcohol at 30–50° C. Excess peroxide is decomposed with aqueous sodium sulfite solution. The organic layer is concentrated and the crude product is purified by flash chromatography on silica gel to afford the title compound.

EXAMPLE 10

Bis[1-(2-hydroxy-1-phenethoxy)-2,2,6,6-tetramethylpiperidin-4-yl] Sebacate

Aqueous hydrogen peroxide is added to a mixture of bis(1-oxyl-2,2,6,6-tetra-methylpieridin-4-yl) sebacate and ferrous chloride tetrahydrate in phenethyl alcohol at 30–50° C. Excess peroxide is decomposed with aqueous sodium sulfite solution. The organic layer is concentrated and the crude product is purified by flash chromatography on silica gel to afford the title compound.

EXAMPLE 11

2,4-Bis {N-[1-(2-hydroxy-2-methylpropoxy)-2,2,6,6-tetramethylpiperidin-4-yl]butylamino}-6-chloro-s-triazine A total of 40 g (0.59 mol) of 50% aqueous hydrogen peroxide is added in two portions over five hours to a mixture of 43.2 g (0.076 mol) of 2,4-bis[N-(1-oxyl-2,2,6,6-tetramethylpiperidin-4-yl)butylamino]-6-chloro-s-triazine and 7.0 g (0.035 mol) of ferrous chloride tetrahydrate in 150 g of tert-butyl alcohol and 15 g of water. Another portion of 50% aqueous hydrogen peroxide (3 g, 0.044 mol) is added to the reaction mixture while the temperature is maintained at 40–45° C. for 2.25 hours. The reaction mixture is diluted with 100 g of ethyl acetate. A solution of 100 g of 20% aqueous sodium sulfite is added and the reaction mixture is heated at 60° C. for one hour to decompose residual peroxide. The aqueous layer is extracted with ethyl acetate, and the combined organic layers are concentrated. The crude product is purified by flash chromatography on silica gel with 1:1 (v/v) hexane/ethyl acetate to afford 54.1 g of the title compound.

EXAMPLE 12 illustrates the use of ferric chloride in the instant process.

EXAMPLE 12

4-Hydroxy-1-(2-hydroxy-2-methylpropoxy)-2,2,6,6-tetramethylpiperidine

A solution of 9.4 g (140 mmol) of 50% aqueous hydrogen peroxide mixed with 20 mL of tert-butyl alcohol is added over four hours at 45–50° C. to a mixture of 3.44 g (20.0 mmol) of 4-hydroxy-1-oxyl-2,2,6,6-tetramethylpiperidine, 0.125 g (0.77 mmol) of anhydrous ferric chloride, 30 mL of tert-butyl alcohol and 10 mL of water. The temperature is then maintained at 45–50° C. for 19 hours. Analysis by gas chromatography shows less than 1% of the starting nitroxyl compound is present.

EXAMPLE 13 shows recycling a metal catalyst on a solid support.

EXAMPLE 13

4-Hydroxy-1-(2-hydroxy-2-methylpropoxy)-2,2,6,6-tetramethylpiperidine 2,2'-Dipyridyl (0.16 g, 1.0 mmol) and 2.54 g (0.80 mmol) of 5% ferric chloride on silica gel are stirred together in 30 mL of tert-butyl alcohol which is heated to 45° C. To the mixture are added 3.44 g (20.0 mmol) of 4-hydroxy-1-oxyl-2,2,6,6-tetramethylpiperidine and 10 mL of water. A solution of 9.4 g (138 mmol) of 50% aqueous hydrogen peroxide mixed with 20 mL of tert-butyl alcohol is added over four hours at 45–50° C. to the reaction mixture. The temperature is maintained at 45–50° C. for 30 minutes. Analysis by gas chromatography shows that the starting nitroxyl compound is completely reacted to form greater than 90% of the title compound.

The silica gel is separated by filtration and the above experiment is repeated using the recovered silica gel. After nearly all the peroxide is added to the reaction mixture in 4.5 hours, gas chromatography shows 36% of the starting nitroxyl compound is still present. After the reaction mixture is heated for an additional 19 hours at 45–50° C., only 5% of the starting nitroxyl compound still remains.

EXAMPLE 14

Reaction of 4-Hydroxy-1-oxyl-2,2,6,6-tetra-methylpiperidine with Isopropyl Alcohol 2,2'-Dipyridyl (0.156 g, 1 mmol) is added to a mixture of 0.20 g (1 mmol) of ferrous chloride tetrahydrate in 30 mL of isopropyl alcohol at 40° C. To this mixture are added 3.44 g (20 mmol) of 4-hydroxy-1-oxyl-2,2,6,6-tetramethylpiperidine and 10 mL of water. A solution of 9.4 g (138 mmol) of 50% aqueous hydrogen peroxide in 20 mL of isopropyl alcohol is added over seven hours at 40–45° C. to the above mixture. The crude reaction mixture is cooled and reacted with 0.5 g of sodium borohydride. Gas chromatography/mass spectrometry analyses indicate the major component of the reaction mixture is 4-hydroxy-1-(2-hydroxypropoxy)-2,2,6,6-tetramethylpiperidine (m/z =231).

EXAMPLE 15

Reaction of 1-Oxyl-2,2,6,6-tetramethyl piperidin-4-one with tert-Amyl Alcohol 2,2'-Dipyridyl (0.078 g, 0.50 mmol) is added to a mixture of 0.99 g (5.0 mmol) of ferrous chloride tetrahydrate is 150 mL of tert-amyl alcohol at 25° C. To this mixture is added 0.2 g of tetrabutylammonium chloride and 17.2 g (101 mmol) of 1-oxyl-2,2,6,6-tetramethylpiperidin-4-one. A solution of 29.5 g (434 mmol) of 50% aqueous hydrogen peroxide is added over three hours at 25–30° C. to the above mixture. Aqueous sodium sulfite solution is added to decompose peroxides. The reaction mixture is thoroughly extracted with ethyl acetate to afford 23.4 g of an orange oil. Gas chromatography/mass spectrometry analyses indicate that the oil contains three major reaction products in a nearly 2:2:1 ratio (area percent). The three products are consistent with the reaction of the starting nitroxyl compound with each of the possible carbon radicals formed from tert-amyl alcohol.

EXAMPLE 16

Reaction of 1-Oxyl-2,2,6,6-tetramethyl piperidin-4-one with 1-Butanol

The procedure of Example 15 is repeated with 150 mL of n-butyl alcohol in place of tert-amyl alcohol. Work-up of the reaction mixture yields 19.2 g of an orange oil. Gas chromatography/mass spectrometry analyses indicate that three of the components of the product mixture correspond to the reaction of the starting nitroxyl compound with radicals formed by hydrogen abstraction from 1-butanol.

EXAMPLE 17

Reaction of 1-Oxyl-2,2,6,6-tetramethyl piperidin-4-one with Neopentyl Glycol The procedure of Example 15 is repeated with a mixture of 400 mL of 2,2-dimethyl1,3-propanediol (=neopentyl glycol) and 55 mL of water in place of tert-amyl alcohol. Work-up of the reaction mixture yields 14.0 g of a brown oil.

EXAMPLE 18

Reaction of 1-Oxyl-2,2,6,6-tetramethyl piperidin-4-one with 2-Octanol

The procedure of Example 15 is repeated with a mixture of 150 mL of 2-octanol in place of tert-amyl alcohol. The peroxide is added over a period of six hours at 25–30° C. and the reaction mixture is stirred overnight at room temperature. Work-up of the reaction mixture gives 19.4 g of an orange oil. Gas chromatography/mass spectrometry analyses indicate that five of the components of the product mixture correspond to the reaction of the starting nitroxyl compound with radicals formed by hydrogen abstraction from 2-octanol.

Examples 19–22 indicate the use of mineral acid with various iron salts in the instant process.

EXAMPLE 19

4-Hydroxy-1-(2-hydroxy-2-methylpropoxy)-2,2,6,6-tetramethylpiperidine

A solution of 17.2 g (100 mmol) of 4-hydroxy-1-oxyl-2,2,6,6-tetramethylpiperidine dissolved in 40 mL of water and three-fourths of a solution of 25.0 g (0.37 mol) of 50% aqueous hydrogen peroxide are added simultaneously over three hours at 40° C. to a mixture of 1.12 g (4.0 mmol) of ferrous sulfate heptahydrate, 25 mL of water, 0.5 mL of 98% sulfuric acid and 200 mL of tert-butyl alcohol. At the conclusion of the nitroxyl addition, 0.145 g (0.5 mmol) of ferrous sulfate heptahydrate, 0.1 mL of 98% sulfuric acid, and 1–2 mL of water are added to the reaction mixture. The remaining one-fourth of the peroxide solution is added over one hour at 40° C. One hour later, a solution of 2.9 g. (40 mmol) of 50% aqueous hydrogen peroxide is added dropwise to the reaction mixture. After another 1.3 hours, a solution of 0.14 g (0.5 mmol) of ferrous sulfate heptahydrate, 0.15 mL of 98% sulfuric acid and 1–2 mL of water are added in one portion. The reaction mixture is stirred an additional 40 minutes at 40° C. After the peroxides are decomposed with sodium sulfite, the reaction mixture is treated with sodium hydroxide and sodium borohydride and concentrated. The residue is dissolved in ethyl acetate and passed through silica gel to afford 20.5 g (84% yield) of the title compound as a white solid.

EXAMPLE 20

4-Hydroxy-1-(2-hydroxy-2-methylpropoxy)-2,2,6,6-tetramethylpiperidine

A solution of 34.5 g (200 mmol) of 4-hydroxy-1-oxyl-2,2,6,6-tetramethylpiperidine dissolved in 75 mL of water and a solution of 49.5 g (0.73 mol) of 50% aqueous hydrogen peroxide are added simultaneously over seven hours at 40° C. to a mixture of 1.61 g (8.1 mmol) of ferrous chloride tetrahydrate, 50 mL of water, 1.6 mL of 37% hydrochloric acid and 390 mL of tert-butyl alcohol. About four hours into the addition, a solution of 0.22 g (1.1 mmol) of ferrous chloride tetrahydrate, 0.2 mL of 37% hydrochloric acid and 1–2 mL of water are added to the reaction mixture. The reaction mixture is stirred overnight at room temperature. The reaction is then completed by adding a solution of 0.11 g (0.55 mmol) of ferrous chloride tetrahydrate, 0.1 mL of 37% hydrochloric acid and 1–2 mL of water and a solution of 5.8 g (85 mmol) of 50% aqueous hydrogen peroxide while heating the reaction mixture at 40° C. The reaction mixture is filtered to remove solids, quenched with sodium sulfite, treated with sodium hydroxide and sodium borohydride and concentrated. The residue is dissolved in ethyl acetate and passed through silica gel to afford 42.6 g (87% yield) of the title compound as a white solid.

EXAMPLE 21

4-Hydroxy-1-(2-hydroxy-2-methylpropoxy)-2,2,6,6-tetramethylpiperidine

A solution of 17.2 g (100 mmol) of 4-hydroxy-1-oxyl-2,2,6,6-tetramethylpiperidine dissolved in 50 mL of water and a solution of 25.3 g (0.37 mol) of 50% aqueous hydrogen peroxide are added simultaneously over 3–3.5 hours at 40° C. to a mixture of 0.27 g (1.0 mmol) of ferric chloride hexahydrate, 25 mL of water, 1.1 mL of 37% hydrochloric acid and 200 mL of tert-butyl alcohol. About two hours into the addition, 0.5 mL of 37% hydrochloric acid is added to the reaction mixture. After the peroxide addition is complete, 1.2 mL of 37% hydrochloric acid is added and the reaction mixture is heated at 40–50° C. for 3.5 hours. The reaction mixture is stirred overnight at room temperature. The reaction is completed by adding two portions of 0.3 mL of 37% hydrochloric acid while heating the reaction mixture at 45° C. for 5.5 hours. Work-up is done as in Example 20 and affords 21.5 g (88% yield) of the title compound as a white solid. Gas chromatography shows the product has a purity greater than 96%.

EXAMPLE 22

4-Hydroxy-1-(2-hydroxy-2-methylpropoxy)-2,2,6,6-tetramethylpiperidine

A solution of 17.2 g (100 mmol) of 4-hydroxy-1-oxyl-2,2,6,6-tetramethylpiperidine dissolved in 40 mL of water and three-fourths of a solution of 25.0 g (0.37 mol) of 50% aqueous hydrogen peroxide are added simultaneously over 2.5 hours to 40° C. to a mixture of 1.46 g (4.1 mmol) of ferric acetylacetonate, 25 mL of water, 0.5 mL of 98% sulfuric acid and 200 mL of tert-butyl alcohol. At the conclusion of the nitroxyl addition, 0.18 g (0.5 mmol) of ferric acetylacetonate is added to the reaction mixture. The remaining one-fourth of the peroxide solution is added over one hour at 40° C. After heating for two hours, gas chromatography shows less than 10% nitroxyl compound remaining in the reaction mixture. Sulfuric acid (0.3 mL) and a solution of 4.9 g (72 mmol) of 50% aqueous hydrogen peroxide are added to the reaction mixture at 40° C., and the reaction mixture is stirred overnight at room temperature. Work-up as in Example 20 affords 18.1 g (74% yield) of the title compound as a white solid.

EXAMPLE 22A

4-Hydroxy-1-(2-hydroxy-2-methylpropoxy)-2,2,6,6-tetramethylpiperidine

When the procedure of Example 22 is repeated without the addition of sulfuric acid, 69% of the starting nitroxyl compound remains present 1.5 hours after the peroxide addition is completed. This compares with only 10% nitroxyl compound remaining at a comparable time as seen in Example 22.

EXAMPLE 23

2,4,6-Tris{N-[1-(2-hydroxy-2-methylpropoxy)-2,2,6,6-tetramethylpiperidin-4-yl]butylamino}-s-triazine A solution of 40 g (0.35 mol) of 30% aqueous hydrogen peroxide is added over 1.25 hours to a mixture of 11.7 g (0.011 mol) of 2,4,6-tris[N-(1-oxyl-2,2,6,6-tetramethylpiperidin-4-yl)butylamino]-s-triazine and 3.0 g (0.015 mol) of ferrous chloride tetrahydrate in 100 g of tert-butyl alcohol and 9 g of water. The reaction temperature is maintained at 60–65° C. during the peroxide addition. Two equal portions (each 2 g, 0.29 mol) of 50% aqueous hydrogen peroxide are added to the reaction mixture while the temperature is maintained at 60° C. for 9.5 hours. After the reaction mixture is diluted with ethyl acetate and cooled to room temperature, a solution of 100 g of 20% aqueous sodium sulfite is added. The reaction mixture is heated at 60° C. for one hour to decompose the excess peroxide. The aqueous layer is extracted with ethyl acetate, and the combined organic layers are concentrated. The crude product is purified by flash chromatography on silica gel with 2:1 (v/v)

cyclohexane/ethyl acetate to afford a material which is triturated with 1:1 (v/v) cyclohexane/acetone to give 4.0 g of the title compound as a white solid, melting at 172–176° C.

EXAMPLE 24

1-(2-Hydroxy-2-methylpropoxy)-2,2,6,6-tetramethylpiperidin-4-one

A solution of 23.6 g (347 mmol) of 50% aqueous hydrogen peroxide is added over 7.5 hours to a mixture of 17.0 g (100 mmol) of 1-oxyl-2,2,6,6-tetramethylpiperidin-4-one, 0.994 g (5 mmol) of ferrous chloride tetrahydrate, 1 mL of 37% hydrochloric acid, 360 mL of tert-butyl alcohol, and 120 mL of water. The reaction is saturated with potassium chloride and the aqueous layer is extracted with tert-butyl alcohol. The combined organic layers are concentrated to an orange oil. The oil is dissolved in methylene chloride and purified by flash chromatography on silica gel with 4:1 (v/v) hexane:ethyl acetate. The resulting yellow oil is crystallized to afford 8.3 g of a white solid melting at 57–60° C. The isolated product is injected into a gas chromatograph and has the same retention time as an authenic sample of the title compound.

Examples 24A, 24B and 24C illustrate the effect of various ligands of formula (IV)

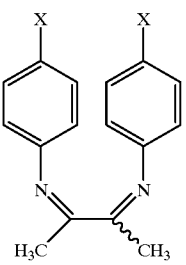

(IV)

on the formation of the compound of Example 24.

EXAMPLE 24A 1-(2-Hydroxy-2-methylpropoxy)-2,2,6,6-tetramethylpiperidin-4-one To a mixture of 0.994 g (5 mmol) of ferrous chloride tetrahydrate and 150 mL of tert-butyl alcohol at 35° C. are added, sequentially, 1.18 g (5.0 mmol) of N,N'-(1,2-dimethyl1,2-ethanediylidene)bis(benzenamine), where in formula IV, X is hydrogen, and 17.0 g (100 mmol) of 1-oxyl-2,2,6,6-tetramethylpiperidin-4-one. A solution of 47.5 g (700 mmol) of 50% aqueous hydrogen peroxide mixed with 60 mL of tert-butyl alcohol is added over eight hours at 35–40° C. to the above mixture. The reaction is stirred an additional 16 hours at 40° C. Analysis by gas chromatography shows less than 4% starting nitroxyl present. Solids are removed by filtration, and the filtrate is reacted with aqueous sodium sulfite to decompose excess peroxide. The reaction mixture is thoroughly extracted with ethyl acetate to afford, after concentration, 21.4 g of crude product containing greater than 93% of the title compound as based on gas chromatography.

EXAMPLE 24B 1-(2-Hydroxy-2-methylpropoxy)-2,2,6,6-tetramethylpiperidin-4-one Example 24A is repeated using 1.48 g (5 mmol) of N,N'-(1,2-dimethyl1,2-ethane-diylidene)bis(4-methoxybenzenamine), where in formula IV, X is methoxy, in place of N,N'-(1,2-dimethyl1,2-ethanediylidene)bis(benzenamine), where in formula IV, X is hydrogen. Analysis by gas chromatography shows 3% starting nitroxyl compound present at the end of the reaction time. After work-up, the reaction mixture affords 17.7 g of an orange material which contains 97% of the title compound as seen by gas chromatography.

EXAMPLE 24C 1-(2-Hydroxy-2-methylpropoxy)-2,2,6,6-tetramethylpiperidin-4-one Example 24A is repeated using 5.0 mmol of N,N'-(1,2-dimethyl1,2-ethane-diylidene)bis(4-chlorobenzenamine), where in formula IV, X is chlorine, in place of N,N'-(1,2-dimethyl1,2-ethanediylidene)bis(benzenamine), where in formula IV, X is hydrogen.

EXAMPLE 25

4-Benzoyloxy-1-(2-hydroxy-2-methylpropoxy)-2,2,6,6-tetramethylpiperidine

A solution of 18.4 g (0.27 mol) of 50% aqueous hydrogen peroxide mixed with 50 mL of tert-butyl alcohol is added over two hours to a mixture of 24.9 g (0.090 mol) of 4-benzoyloxy-1-oxyl-2,2,6,6-tetramethylpiperidine, 7.13 g (0.036 mol) of ferrous chloride tetrahydrate, 3.7 g (0.030 mol) of picolinic acid, and 150 mL of tert-butyl alcohol at 60° C. The reaction temperature is maintained at 60° C. for five hours after the peroxide addition is complete. The reaction mixture is filtered to remove solids, and the filtrate is stirred for 30 minutes with 1 liter of 10% aqueous sodium sulfite solution to decompose excess peroxide. The aqueous solution is extracted three times with methylene chloride, and the combined organic layers are dried over anhydrous magnesium sulfate and finally concentrated to an orange oil. Purification by flash chromatography on silica gel with 4:1 (v/v) hexane:ethyl acetate affords 12.0 g of an amber oil. The product is confirmed to be the title compound by nmr and mass spectrometry analyses.

Example 25A shows the effect of omitting the picolinic acid from Example 25.

EXAMPLE 25A

4-Benzoyloxy-1-(2-hydroxy-2-methylpropoxy)-2,2,6,6-tetramethylpiperidine

A solution of 20.4 g (0.30 mol) of 50% aqueous hydrogen peroxide mixed with 25 mL of tert-butyl alcohol is added over three hours to a mixture of 27.6 g (0.10 mol) of 4-benzoyloxy-1-oxyl-2,2,6,6-tetramethylpiperidine, 7.13 g (0.036 mol) of ferrous choride tetrahydrate and 115 mL of tert-butyl alcohol at 40° C. The reaction temperature is maintained at 40° C. for twenty hours after the peroxide addition is complete. The crude reaction mixture is purified by flash chromatography on silica gel to afford 16.2 g of the title compound.

EXAMPLE 26

Reaction of Bis(1-oxyl-2,2,6,6-tetramethylpiperidin-4-yl) Sebacate with Neopentyl alcohol Aqueous hydrogen peroxide is added to a mixture of bis(1-oxyl-2,2,6,6-tetra-methylpiperidin-4-yl) sebacate and ferrous chloride in neopentyl alcohol according to the procedure of Example 25A.

EXAMPLE 27

Reaction of 4-Hydroxy-1-oxyl-2,2,6,6-tetramethylpiperidine with Neopentyl Glycol Aqueous hydrogen peroxide is added to a mixture of 4-hydroxy-1-oxyl-2,2,6,6-tetramethylpiperidine and ferrous chloride in neopentyl glycol according to the procedure of EXAMPLE 25A.

EXAMPLE 28

Reaction of 4-Octadecanoyloxy-1-oxyl-2,2,6,6-piperidine with tert-Amyl Alcohol

Aqueous hydrogen peroxide is added to a mixture of 4-octadecanoyloxy-1-oxyl-2,2,6,6-tetramethylpiperidine and ferrous chloride in tert-amyl alcohol according to the procedure of Example 25A.

EXAMPLE 28A

Reaction of 4-Octadecanoyloxy-1-oxyl-2,2,6,6-piperidine with tert-Butyl Alcohol

Aqueous hydrogen peroxide is added to a mixture of 4-octadecanoyloxy-1-oxyl-2,2,6,6-tetramethylpiperidine and ferrous chloride in tert-butyl alcohol according to the procedure of Example 25A.

EXAMPLE 29

Reaction of 4-Benzoyloxy-1-oxyl-2,2,6,6-tetramethylpiperidine with Propylene Glycol Aqueous hydrogen peroxide is added to a mixture of 4-benzoyloxy-1-oxyl-2,2,6,6-tetramethylpiperidine and ferrous chloride tetrahydrate in propylene glycol according to the procedure of Example 25A.

EXAMPLE 30

Reaction of 1-Oxyl-2,2,6,6-tetramethyl piperidin-4-one with Trimethylene Glycol

Aqueous hydrogen peroxide is added to a mixture of 1-oxyl-2,2,6,6-tetramethylpiperidine-4-one and ferrous chloride tetrahydrate in trimethylene glycol according to the procedure of Example 25A.

EXAMPLE 31

Reaction of Bis(1-oxyl-2,2,6,6-tetramethylpiperidin-4-yl) Sebacate with 2-Propanol Aqueous hydrogen peroxide is added to a mixture of bis(1-oxyl-2,2,6,6-tetra-methylpiperidin-4-yl) sebacate and ferrous chloride tetrahydrate in 2-propanol according to the procedure of Example 25A.

EXAMPLE 32

Reaction of 4-Benzoyloxy-1-oxyl-2,2,6,6-tetramethylpiperidine with 1,4-Butanediol Aqueous hydrogen peroxide is added to a mixture of 4-benzoyloxy-1-oxyl-2,2,6,6-tetramethylpiperidine and ferrous chloride tetrahydrate in 1,4-butanediol according to the procedure of Example 25A.

EXAMPLE 33

Reaction of 4-Hexyloxy-1-oxyl-2,2,6,6-tetramethylpiperidine with Pinacol

Aqueous hydrogen peroxide is added to a mixture of 4-hexyloxy-1-oxyl-2,2,6,6-tetramethylpiperidine and ferrous chloride tetrahydrate in pinacol according to the procedure of Example 25A.

EXAMPLE 34

Reaction of 4-Hydroxy-1-oxyl-2,2,6,6-tetramethylpiperidine with 2-Ethyl1-hexanol Aqueous hydrogen peroxide is added to a mixture of 4-hydroxy-1-oxyl-2,2,6,6-tetramethylpiperidine and ferrous chloride tetrahydrate in 2-ethyl1-hexanol according to the procedure of Example 25A.

EXAMPLE 35

Reaction of N,N',N'',N'''-Tetrakis{2,4-bis[N-(1-oxyl-2,2,6,6-tetramethylpiperidin-4-yl)butylamino]-s-triazin-6-yl}-3,3'-ethylenediiminodipropylamine with Cyclohexanol A mixture of N,N',N'',N'''-tetrakis(2,4-bis[N-(1-oxyl-2,2,6,6-tetramethylpiperidin-4-yl)butylamino]-s-triazin-6-yl}-3,3'-ethylenediiminodipropylamine in cyclohexanol is reacted with aqueous hydrogen peroxide and ferrous chloride tetrahydrate according to the method of Example 4. A white solid melting at 133–175° C. is obtained.

EXAMPLE 36

Reaction of 2,4,6-Tris[N-(1-oxyl-2,2,6,6-tetramethylpiperidin-4-yl)butylamino]-s-triazine with Cyclohexanol A mixture of 2,4,6-tris[N-(1-oxyl-2,2,6,6-tetramethylpiperidin-4-yl)butylamino]-s-triazine and cyclohexanol is reacted with aqueous hydrogen peroxide and ferrous chloride tetrahydrate according to the procedure of Example 4. A light brown oil is obtained.

EXAMPLE 37

N,N',N'',N'''-Tetrakis (2,4-bis[N-[1-(2-hydroxy-2-methylpropoxy)-2,2,6,6-tetramethylpiperidin-4-yl]butylamino]-s-triazin-6-yl)-3,3'-ethylenediiminodipropylamine The title compound is prepared by the addition of aqueous hydrogen peroxide to a mixture of N,N',N'',N'''-tetrakis{2,4-bis[N-(1-oxyl-2,2,6,6-tetramethylpiperidin-4-yl)butylamino]-s-triazin-6-yl}-3,3'-ethylenediiminodipropylamine, ferrous chloride and tert-butyl alcohol according to the procedure of Example 7.

EXAMPLE 37A

N,N',N'''-Tris {2,4-bis[N-[1-(2-hydroxy-2-methylpropoxy)-2,2,6,6-tetramethylpiperidin-4-yl]butylamino]-s-triazin-6-yl }-3,3'-ethylenediiminodipropylamine The title compound is prepared by the addition of aqueous hydrogen peroxide to a mixture of N,N',N'''-tris{2,4-bis[N-(1-oxyl-2,2,6,6-tetramethylpiperidin-4-yl)butyl-amino]-s-triazin-6-yl)}-3,3'-ethylenediiminodipropylamine, ferrous chloride and tert-butyl alcohol according to the procedure of Example 7.

EXAMPLE 37B

N,N',N'''-Tris{2,4-bis[N-[1-(2-hydroxy-2-methylpropoxy)-2,2,6,6-tetramethylpiperidin-4-yl]butylamino]-s-triazin-6-yl)}-3,3'-ethylenediiminodipropylamine The title compound is prepared by the addition of aqueous hydrogen peroxide to a mixture of N,N',N'''-tris{2,4-bis

[N-(1-oxyl-2,2,6,6-tetramethylpiperidin-4-yl)butyl-amino]-s-triazin-6-yl)}-3,3'-ethylenediiminodipropylamine, ferrous chloride and tert-butyl alcohol according to the procedure of Example 7.

Examples 38–47 show the effectiveness of various metals in the instant process.

EXAMPLE 38

4-Hydroxy-1-(2-hydroxy-2-methylpropoxy)-2,2,6,6-tetramethylpiperidine

A solution of 50% aqueous hydrogen peroxide is added at a rate of approximately 100 mmol per hour and, simultaneously, a solution of 17.2 g (100 mmol) of 4-hydroxy-1-oxyl-2,2,6,6-tetramethylpiperidine dissolved in 40–45 mL of water is added at a rate of 35–50mmol per hour to a mixture of metal salt, acid if used, 25 mL of water and 200 mL of tert-butyl alcohol maintained at 35–45° C. The reaction mixture is maintained at 35–45° C. after all reactants are added, and in some cases the reaction mixture is stirred overnight at room temperature. The reaction is monitored by gas chromatography. Results are tabulated below.

TABLE I

Formation of 4-Hydroxy-1-(2-hydroxy-2-methylpropoxy)-2,2,6,6-tetramethylpiperidine Using Hydrogen Peroxide and Various Metals

| mol % metal[a] | mol % acid[a] | moles $H_2O_2$[b] | yield[c] |
|---|---|---|---|
| 4% $CoCl_2$ | 10% HCl | 2.9 | 3% |
| 11% $MnCl_2$ | 10% HCl | 3.6 | 16% |
| 4% $NaVO_3$ | none | 1.5 | <1% |
| 4% $CeCl_3$ | none | 1.5 | <1% |
| 4% $TiCl_3$ | 60% HCl | 3.5 | 2% |
| 4% $VCl_2$ | 10% HCl | 2.2 | 1% |
| 4% $VCl_3$ | 10% HCl | 3.6 | 6% |

(a) moles per mole of nitroxyl starting material;
(b) moles of peroxide added to reaction per mole of nitroxyl starting material; and
(c) gas chromatographic yields based on integrated area of title compound with respect to total area of all hindered amine components present in the reaction mixture.

EXAMPLE 39

1-(2-Hydroxy-2-methylpropoxy)-2,2,6,6-tetramethylpiperidin-4-one

A solution of 1.0 g (15 mmol) of 50% aqueous hydrogen peroxide is added in 5 mL of tert-butyl alcohol over 30 minutes at 60° C. to a mixture of 0.5 g (2.9 mmol) of 1-oxyl-2,2,6,6-tetramethylpiperidin-4-one, 0.1 g (0.16 mmol) of N,N'-bis(3,5-di-tert-butylsalicylidene)-1,2-cyclohexanediaminomanganese(II) chloride (Jacobsen's catalyst), and 10 mL of tert-butyl alcohol. The reaction is stirred overnight at 60° C. Gas chromatography shows 2.5% of the title compound is present in the reaction mixture.

EXAMPLE 40

1-(2-Hydroxy-2-methylpropoxy)-2,2,6,6-tetramethylpiperidin-4-one

The procedure of Example 39 is repeated using 0.25 g (1.05 mmol) of cobalt(II) chloride hexahydrate in place of the Jacobsen's catalyst. Gas chromatography shows 9% of the title compound is present in the reaction mixture.

EXAMPLE 41

4-Hydroxy-1-(2-hydroxy-2-methylpropoxy)-2,2,6,6-tetramethylpiperidine

A solution of 0.25 g (1.0 mmol) of copper(II) sulfate pentahydrate in 5 mL of water is added to a solution of 0.16 g (1.0 mmol) of 2,2'-dipyridyl in 120 mL of tert-butyl alcohol. To this solution is added 8.6 g (50 mmol) of 4-hydroxy-1-oxyl-2,2,6,6-tetramethylpiperidine. A solution of 13.6 g (200 mmol) of 50% aqueous hydrogen peroxide mixed with 13 mL of tert-butyl alcohol is added dropwise to the reaction mixture at 23–40° C. over three hours. The mixture is then stirred at ambient temperature for 72 hours. Gas chromatography shows 9% of the title compound is present in the reaction mixture.

EXAMPLE 42

4-Hydroxy-1-(2-hydroxy-2-methylpropoxy)-2,2,6,6-tetramethylpiperidine

A solution of 34.5 g (200 mmol) of 4-hydroxy-1-oxyl-2,2,6,6-tetramethylpiperidine dissolved in 75 mL of water and a solution of 48.1 g (0.71 mol) of 50% aqueous hydrogen peroxide are added simultaneously over six hours at 35–45° C. to a mixture of 0.79 g (8.0 mmol) of copper(1) chloride, 50 mL of water, 1.6 mL of 37% hydrochloric acid, and 400 mL of tert-butyl alcohol. The reaction mixture is stirred overnight at room temperature. The reaction mixture is heated to 40–45° C. and treated with a total of 1.78 g of copper(I) chloride, 4.4 mL of 37% hydrochloric acid, and 85 g (1.25 mol) of 50% aqueous hydrogen peroxide to react completely the remaining nitroxyl compound. Work-up according to the procedure of Example 20 affords 38.6 g of a tan solid containing 88% of the title compound based on gas chromatographic analysis.

EXAMPLE 43

4-Hydroxy-1-(2-hydroxy-2-methylpropoxy)-2,2,6,6-tetramethylpiperidine

A solution of 17.2 g (100 mmol) of 4-hydroxy-1-oxyl-2,2,6,6-tetramethylpiperidine dissolved in 50 mL of water and a solution of 31.5 g (0.46 mol) of 50% aqueous hydrogen peroxide are added simultaneously over three and 4.5 hours respectively to a mixture of 0.69 g (4.0 mmol) of copper(II) chloride dihydrate, 25 mL of water, 0.8 mL of 37% hydrochloric acid, and 200 mL of tert-butyl alcohol at 35–50° C. The reaction mixture is maintained at 45–50° C. and treated with a total of 0.32 g of copper(II) chloride dihydrate, 0.6 mL of 37% hydrochloric acid, and 35.5 g (0.52 mol) of 50% aqueous hydrogen peroxide to react completely the remaining nitroxyl compound. Work-up according to the method of Example 20 affords 17.1 g of an off-white solid containing 90% of the title compound based on gas chromatographic analysis.

EXAMPLE 44

4-Hydroxy-1-(2-hydroxy-2-methylpropoxy)-2,2,6,6-tetramethylpiperidine

A solution of 17.2 g (100 mmol) of 4-hydroxy-1-oxyl-2,2,6,6-tetramethylpiperidine dissolved in 50 mL of water and a solution of 29.3 g (0.43 mol) of 50% aqueous hydrogen peroxide are added simultaneously over three and 4.25 hours respectively to a mixture of 1.0 g (4.0 mmol) of copper(II) sulfate pentahydrate, 25 mL of water, 0.6 mL of 98% sulfuric acid, and 200 mL of tert-butyl alcohol at 35–50° C. The reaction mixture is maintained at 45–50° C. and treated with a total of 0.44 g of copper(II) sulfate pentahydrate, 0.4 mL of 98% sulfuric acid, and 6.7 g (98 mmol) of 50% aqueous hydrogen peroxide to react completely the remaining nitroxyl compound. Work-up according to the method of

EXAMPLE 20 affords 19.1 g of a white solid containing 95% of the title compound based on gas chromatographic analysis.

EXAMPLE 45

4-Hydroxy-1-(2-hydroxy-2-methylpropoxy)-2,2,6,6-tetramethylpiperidine

A solution of 7.4 g (109 mmol) of 50% aqueous hydrogen peroxide in 10 mL of water is added dropwise over five hours at 43–60° C. to a mixture prepared by the sequential addition of 5 mL of water, 0.5 mL of glacial acetic acid, 60 mL of tert-butyl alcohol and a solution of 5.4 g (31.4 mmol) of 4-hydroxy-1-oxyl-2,2,6,6-tetramethylpiperidine in 5 mL of water to 0.166 g (0.95 mmol) of ferrous acetate. A fresh solution of 4.4 g (65 mmol) of 50% aqueous hydrogen peroxide and 4 mL of water is then added to the reaction mixture at 60° C. The mixture is stirred overnight at room temperature.

Analysis by gas chromatography shows that the reaction mixture contains 52% of the title compound and 41% unreacted starting material based on the original nitroxyl content.

EXAMPLE 46

4-Hydroxy-1-(2-hydroxy-2-methylpropoxy)-2,2,6,6-tetramethylpiperidine

The procedure of Example 20 is repeated using a mixture of ferrous chloride and ferric chloride.

EXAMPLE 47

4-Hydroxy-1-(2-hydroxy-2-methylpropoxy)-2,2,6,6-tetramethylpiperidine

The procedure of Example 20 is repeated using a mixture of ferric chloride and iron powder in place of ferrous chloride.

Examples 48 and 49 show the reaction where tert-butyl hydroperoxide is used in place of hydrogen peroxide.

EXAMPLE 48

4-Hydroxy-1-(2-hydroxy-2-methylpropoxy)-2,2,6,6-tetramethylpiperidine

A solution of 5.2 g (30 mmol) of 4-hydroxy-1-oxyl-2,2,6,6-tetramethylpiperidine dissolved in 20 mL of water and a solution of 7.8 g (61 mmol) of 70% aqueous tert-butyl hydroxperoxide are added simultaneously over one hour at 35–50° C. to a mixture of 0.33 g (1.2 mmol) of ferric chloride hexahydrate, 8 mL of water, 0.2 mL of 37% hydrochloric acid, and 60 mL of tert-butyl alcohol. The reaction mixture is maintained at 45° C. for one hour after the addition and is then stirred at room temperature for three days. Gas chromatography shows 3% of the title compound is present in the reaction mixture.

EXAMPLE 49

4-Hydroxy-1-(2-hydroxy-2-methylpropoxy)-2,2,6,6-tetramethylpiperidine

The procedure of Example 48 is repeated using ferrous chloride in place of ferric chloride.

EXAMPLE 50

4-Hydroxy-1-(2-hydroxy-2-methylpropoxy)-2,2,6,6-tetramethylpiperidine

This example uses the addition compound formed from urea and hydrogen peroxide in place of 50% aqueous hydrogen peroxide.

A solution of 52.2 g (555 mmol) of urea-hydrogen peroxide addition compound dissolved in 75 mL of water and a solution of 3 mL of concentrated sulfuric acid dissolved in 29 mL of water are prepared. Portions of both solutions are added simultaneously over two hours at a temperature of 40° C. to a mixture of 0.17 g (61 mmol) of ferrous sulfate heptahydrate, 34.75 g (202 mmol) of 4-hydroxy-1-oxyl-2, 2,6,6-tetramethylpiperidine, 410 mL of tert-butyl alcohol and 70 mL of water. A fresh portion of 0.485 g of ferrous sulfate heptahydrate is added and the reaction mixture is stirred overnight at 45° C. for 16 hours. The remaining peroxide and acid solutions are added simultaneously to the reaction mixture over seven hours at 45° C. Concentrated sulfuric acid (1.8 mL) is added and the mixture is stirred at room temperature for 64 hours. After the reaction mixture is heated at 45–50° C. for 6.5 hours, 1.8 mL of concentrated sulfuric acid and 0.101 g of ferrous sulfate heptahydrate are added. The reaction mixture is then heated at 45° C. for 16 hours to bring the nitroxyl concentration to less than 1% of its original value. The reaction mixture is worked up following the procedure similar to that described in Example 20 to afford 38.1 g (77% yield) of product as a white solid.

Anaylsis by gas chromatography shows the reaction product contains approximately 94% of the title compound.

EXAMPLE 51

4-Hydroxy-1-(2-hydroxy-2-methylpropoxy)-2,2,6,6-tetramethylpiperidine

Examples 51–54 show the effect of different acids on the instant process.

A solution of 17.2 g (100 mmol) of 4-hydroxy-1-oxyl-2, 2,6,6-tetramethylpiperidine in 35 mL of water and a solution of 23.3 g (342 mmol) of 50% aqueous hydrogen peroxide are added simultaneously over 2.5 hours and 6.5 hours, respectively, to a mixture of 0.527 g (3.0 mmol) ferrous acetate, 20 mL of water, 2.3 g of trifluoroacetic acid, and 200 mL of tert-butyl alcohol which is maintained at 43° C. Near the end of the peroxide addition, a solution of 0.347 g (2.0 mmol) of ferrous acetate and 1.25 g of trifluoroacetic acid in 5 mL of water is added to the mixture. A fresh portion of 5.1 g (75 mmol) of 50% aqueous hydrogen peroxide is then added over 90 minutes, and the reaction mixture is stirred for 15 hours at 42–45° C. The reaction mixture is worked up following a procedure similar to that described in Example 20 to afford 17.5 g (71% yield) of product as a white solid.

Analysis by gas chromatography shows the reaction product contains approximately 92% of the title compound.

EXAMPLE 52

4-Hydroxy-1-(2-hydroxy-2-methylpropoxy)-2,2,6,6-tetramethylpiperidine

A solution of 17.2 g (100 mmol) of 4-hydroxy-1-oxyl-2, 2,6,6-tetramethylpiperidine in 35 mL of water and a solution of 31.6 g (464 mmol) of 50% aqueous hydrogen peroxide are added simultaneously over 2.5 hours and 15 hours, respectively, to a mixture of 0.561 g (3.1 mmol) of ferrous oxalate dihydrate, 20 mL of water, 1.26 g of oxalic acid dihydrate, and 200 mL of tert-butyl alcohol which is maintained at 43–65° C. After the peroxide is added, the reaction mixture is stirred for seven hours at 50–60° C. Oxalic acid dihydrate (1.26 g) and 0.380 g (2.2 mmol) of ferrous oxalate dihydrate are added to the reaction mixture and stirring is continued at 65–80° C. for seven hours.

Analysis by gas chromatography shows the reaction mixture comprises approximately 86% of the title compound and less than 4% of the starting material based on hindered amine content.

EXAMPLE 53

4-Hydroxy-1-(2-hydroxy-2-methylpropoxy)-2,2,6,6-tetramethylpiperidine

A solution of 17.2 g (100 mmol) of 4-hydroxy-1-oxyl-2,2,6,6-tetramethylpiperidine in 35 mL of water and a solution of 23.4 g (344 mmol) of 50% aqueous hydrogen peroxide are added simultaneously over 2.5 hours and 6 hours, respectively, to a mixture of 0.563 g (2.0 mmol) ferrous sulfate heptahydrate, 10 mL of water, 1.3 mL of methanesulfonic acid, and 200 mL of tert-butyl alcohol which is maintained at 45° C. The reaction mixture is stirred at 45° C. for two hours after the completion of the peroxide addition.

Analysis by gas chromatography shows the reaction mixture comprises 85% of the title compound and less than 2% of the starting material based on hindered amine content.

EXAMPLE 54

4-Hydroxy-1-(2-hydroxy-2-methylpropoxy)-2,2,6,6-tetramethylpiperidine

A solution of 46.5 g (270 mmol) of 4-hydroxy-1-oxyl-2,2,6,6-tetramethylpiperidine in 120.5 g of tert-butyl alcohol and 108 mL of water and a solution of 37.4 g (550 mmol) of 50% aqueous hydrogen peroxide are added simultaneously over 3 hours and 11.5 hours, respectively, to a mixture of 3.5 g (12.9 mmol) ferric chloride heptahydrate, 32 mL of water, 1.3 g of 85% phosphoric acid, and 292 mL of tert-butyl alcohol which is maintained at 80° C. The reaction mixture is maintained at 80° C. for 30 minutes after completion of the peroxide addition.

Analysis by gas chromatography shows less than 1% of the starting nitroxyl compound remains. Excess peroxide is destroyed by sodium sulfite and the crude product is filtered and treated with sodium borohydride in 14 molar aqueous sodium hydroxide to afford 71% yield of the title compound as analyzed by gas chromatography.

EXAMPLE 55

4-Hydroxy-1-(2-hydroxy-2-methylpropoxy)-2,2,6,6-tetramethylpiperidine

This example shows that a solution of the metal salt can be added dropwise to the reaction mixture throughout the course of the reaction.

A solution of 1.62 g (8.1 mmol) of ferrous chloride tetrahydrate, 2 mL of 37% hydrochloric acid, and 50 mL of water and a solution of 35.7 g (525 mmol) of 50% aqueous hydrogen peroxide are added simultaneously over 13 hours and 16 hours, respectively, to a mixture of 34.5 g (200 mmol) of 4-hydroxy-1-oxyl-2,2,6,6-tetramethylpiperidine in 100 mL of water and 400 mL of tert-butyl alcohol which is maintained at a temperature of 38–45° C. The reaction mixture is heated at 40–45° C. for eight hours after completion of the peroxide addition.

Analysis by gas chromatography shows that the reaction mixture contains 86% of the title compound and less than 5% of the starting nitroxyl compound.

EXAMPLE 56

4-Hydroxy-1-(2-hydroxy-2-methylpropoxy)-2,2,6,6-tetramethylpiperidine

Examples 56–57 show the effect of increasing the reaction temperature.

A solution of 2 mL of 98% sulfuric acid in 30 mL of water and a solution of 27.1 g (398 mmol) of 50% aqueous hydrogen peroxide are added simultaneously over 5.5 hours to a solution of 0.119 g (0.43 mmol) of ferrous sulfate heptahydrate, 70 mL of water, 34.6 g (201 mmol) of 4-hydroxy-1-oxyl-2,2,6,6-tetramethylpiperidine and 410 mL of tert-butyl alcohol which is maintained at a temperature of 43–45° C. The reaction mixture is heated at 45° C. for 20 hours after completion of the peroxide addition.

Analysis by gas chromatography shows that the reaction mixture contains 73% of the title compound and 18% of the starting nitroxyl compound.

EXAMPLE 57

4-Hydroxy-1-(2-hydroxy-2-methylpropoxy)-2,2,6,6-tetramethylpiperidine

A solution of 27.7 g (407 mmol) of 50% aqueous hydrogen peroxide and 90% of a solution of 2.2 mL of 98% sulfuric acid in 30 mL of water are added simultaneously over 5.25 hours and 6.5 hours, respectively, to a solution of 0.115 g (0.41 mmol) of ferrous sulfate heptahydrate, 70 mL of water, 34.6 g (201 mmol) of 4-hydroxy-1-oxyl-2,2,6,6-tetramethylpiperidine and 410 mL of tert-butyl alcohol which is maintained at a temperature of 63–68° C. All of the peroxide is consumed after 6.5 hours.

Analysis by gas chromatography shows that the reaction mixture contains 76% of the title compound and 12% of the starting nitroxyl compound.

EXAMPLE 58

4-Hydroxy-1-(2-hydroxy-2-methylpropoxy)-2,2,6,6-tetramethylpiperidine

A solution of 10.0 g (58.1 mmol) of 4-hydroxy-1-oxyl-2,2,6,6-tetramethylpiperidine in 20 mL of water and a solution of 15 g (220 mmol) of 50% aqueous hydrogen peroxide are added simultaneously over 1.5 hours and 7 hours, respectively, to a solution of 0.394 g (1.77 mmol) of ferric phosphate tetrahydrate, 13 mL of water, and 120 mL of tert-butyl alcohol which is maintained at a temperature of 63–81° C. The reaction mixture is stirred overnight at room temperature. A fresh portion of 1.0 g (15 mmol) of 50% aqueous hydrogen peroxide is added, and the reaction mixture is stirred for 24 hours at 80° C. to bring the amount of the nitroxyl compound to less than 1.5% of the original amount. Excess peroxide is decomposed with sodium sulfite.

Analysis by gas chromatography shows the reaction mixture contains approximately 89% of the title compound based on total hindered amine content.

EXAMPLE 59

4-Hydroxy-1-(2-hydroxy-2-methylpropoxy)-2,2,6,6-tetramethylpiperidine

A solution of 10.1 g (58.7 mmol) of 4-hydroxy-1-oxyl-2,2,6,6-tetramethylpiperidine in 30 mL of water and a solution of 16.3 g (240 mmol) of 50% aqueous hydrogen peroxide are added simultaneously over 2 hours and 6 hours, respectively, to a solution of 1.31 g (1.76 mmol) of ferric pyrophosphte, 20 mL of water, and 120 mL of tert-butyl alcohol which is maintained at a temperature of 60–79° C. The reaction mixture is stirred overnight at room temperature. To the reaction mixture are added a solution of 15 mL of tert-butyl alcohol, 0.34 g (0.46 mmol) of ferric pyrophosphate, and 3.8 g (56 mmol) of 50% aqueous hydrogen peroxide. The mixture is then heated for ten hours at 75–80° C. Excess peroxide is decomposed with sodium sulfite. The reaction mixture is worked up in a procedure similar to that described in Example 20 to afford 10.2 g (71% yield) of product as a white solid which is consistent with the title compound according to gas chromatography analysis.

EXAMPLE 60

4-Hydroxy-1-(2-hydroxy-2-methylpropoxy)-2,2,6,6-tetramethylpiperidine

This example illustrates the effect of combining two different metal salts in the instant process.

A solution of 0.13 g (0.52 mmol) of cupric sulfate pentahydrate, 1mL of 98% sulfuric acid, and 15 mL of water and a solution of 13.6 g (200 mmol) of 50% aqueous hydrogen peroxide are added simultaneously over 3.5 hours and 4.25 hours, respectively, to a solution prepared by the addition of 17.4 g (101 mmol) of 4-hydroxy-1-oxyl-2,2,6,6-tetramethylpiperidine in 50 mL of water to a mixture of 0.14 g (0.50 mmol) of ferrous sulfate heptahydrate, 10 mL of water and 200 mL of tert-butyl alcohol. The reaction mixture is kept at 40–45° C. during the addition, and then stirred overnight at room temperature.

Analysis by gas chromatography shows that 77% of the starting compound is converted to the title compound.

EXAMPLE 61

Mixture of Bis[1-(2-hydroxy-2-methylpropoxy)-2,2,6,6-tetramethylpiperidin-4-yl] Adipate and Bis[1-(2-hydroxy-2-methylpropoxy)-2,2,6,6-tetramethylpiperidin-4-yl] Glutarate A solution of 159 g (2.34 mol) of 50% aqueous hydrogen peroxide is added dropwise to a mixture of 168.4 g of a mixture of bis[1-oxyl-2,2,6,6-tetramethylpiperidin-4-yl] adipate and bis[1-oxyl-2,2,6,6-tetramethylpiperidin-4-yl] glutarate prepared from DBE-30® (dibasic ester, DuPont having approximately 9:1 dimethyl adipate:dimethyl glutarate), 2.03 g (7.5 mmol) of ferric chloride hexahydrate, 1.5 mL of 37% hydrochloric acid, 1.9 mL of tert-butyl alcohol and 262 mL of water at a temperature of 40° C. After a total reaction time of 30 hours, the temperature is increased to 70° C. and a solution of 71 g (1.04 mol) of 50% aqueous hydrogen peroxide is added to the mixture over six hours. After the mixture is stirred for 13 hours at 65° C., another 71 g portion of 50% aqueous hydrogen peroxide is added over six hours, and the mixture is stirred at 65° C. for 17 hours. Excess peroxide is decomposed with sodium sulfite. The mixture is filtered to remove solids, and most of the tert-butyl alcohol and water are removed by co-distillation with heptane. The residue is extracted with ethyl acetate, and the solution is washed with saturated sodium chloride solution. Solvent is evaporated, and the residue is purified by flash chromatography on silica gel with hexane/ethyl acetate to afford 84.1 g of a white solid melting at 131.5–133° C. A second crop of 16.3 g of a white solid melting at 128–130° C. is also obtained.

NMR analysis shows the structure of the white solid to be consistent with the expected adipate/glutarate reaction product.

EXAMPLE 62

Mixture of Bis[1-(2-hydroxy-2-methylpropoxy)-2,2,6,6-tetramethylpiperidin-4-yl] Adipate and Bis[1-(2-hydroxy-2-methylpropoxy)-2,2,6,6-tetramethylpiperidin-4-yl] Glutarate The procedure outlined in Example 61 is repeated using a mixture of bis[1-oxyl-2,2,6,6-tetramethylpiperidin-4-yl] adipate and bis[1-oxyl-2,2,6,6-tetramethylpiperidin- 4-yl] glutarate prepared from DBE-20® (dibasic ester, DuPont having approximately 3:7 dimethyl adipate:dimethyl glutarate) in place of bis[1-oxyl-2,2,6,6-tetramethylpiperidin-4-yl] adipate and bis[1-oxyl-2,2,6,6-tetramethylpiperidin-4-yl] glutarate prepared from DBE-30® described in Example 61.

EXAMPLE 63

4-Hydroxy-1-(2-hydroxy-2-methylpropoxy)-2,2,6,6-tetramethylpiperidine

A solution of 34.6 g (201 mmol) of 4-hydroxy-1-oxyl-2,2,6,6-tetramethylpiperidine in 50 mL of water and a solution of 25.2 g (370 mmol) of 50% aqueous hydrogen peroxide are added simultaneously over four hours and eight hours, respectively, to a mixture of 1.12 g (4.0 mmol) of ferrous sulfate heptahydrate, 20 mL of water and 1mL of methanesulfonic acid and 400 mL of tert-butyl alcohol which is maintained at 80–85° C. A solution of 0.506 g (1.8 mmol) of ferrous sulfate heptahydrate and 0.3 mL of methanesulfonic acid in 2 mL of water is added to the reaction mixture during the peroxide addition. The mixture is stirred at 80–85° C. for 30 minutes after the peroxide is added. Gas chromatography shows that less than 1% of the starting nitroxyl remains. The reaction is worked up following a procedure similar to that of Example 20 to afford 40.8 g of a white solid which contains 98% of the title compound by gas chromatography analysis.

What is claimed is:

1. A process for preparing a compound of formula I

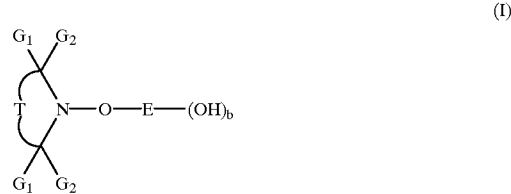

(I)

wherein $G_1$ and $G_2$ are independently alkyl of 1 to 4 carbon atoms, or $G_1$ and $G_2$ together are pentamethylene;

T is a divalent organic radical required to complete a five- or six-membered ring containing the hindered amine nitrogen atom and two quaternary carbon atoms substituted by $G_1$ and $G_2$;

E is a (b+1) valent alkylene radical of 2 to 18 carbon atoms, an alkenylene radical of 3 to 19 carbon atoms, a cycloalkylene radical of 5 to 12 carbon atoms, a cycloalkenylene radical of 5 to 12 carbon atoms or an alkylene radical of 2 to 4 carbon atoms substituted by phenyl or by phenyl substituted by one or two alkyl of 1 to 4 carbon atoms; and b is 1, 2 or 3; with the proviso that b cannot exceed the number of saturated carbon atoms in E, and when b is 2 or 3, each hydroxyl group is bonded to a different carbon atom in E;

which process comprises reacting a N-oxyl hindered amine of formula II

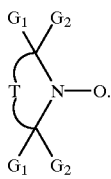

with an alcohol of formula III

in the presence of a peroxide or organic hydroperoxide and a catalytic amount of a metal salt or metal-ligand complex.

2. A process according to claim 1 where $G_1$ and $G_2$ are each methyl.

3. A process according to claim 1 where T is 2-hydroxy-1,3-propanediyl or 2-oxo-1,3-propanediyl.

4. A process according to claim 1 where, when b is 1,
—E—(OH) is a carbon centered radical formed from 2-methyl2-propanol (=tert-butyl alcohol), 2-propanol, 2,2-dimethyl1-propanol, 2-methyl2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl1-hexanol, 2-octanol, cyclohexanol, cyclooctanol, allyl alcohol, phenethyl alcohol or 1-phenyl-1-ethanol.

5. A process according to claim 4 wherein —E—(OH) is formed from 2-methyl2-propanol (=tert-butyl alcohol) or cyclohexanol.

6. A process according to claim 1 where, when b is 2,
—E—(OH)$_2$ is a carbon centered radical formed from 1,2-propanediol, 1,3-propanediol, 1,2-butanediol, 1,4-butanediol, 2,2-dimethyl1,3-propanediol, 2,5-dimethyl2,5-hexanediol, 1,2-cyclohexanediol, 1,3-cyclohexanediol or 1,4-cyclohexanediol.

7. A process according to claim 6 wherein —E—(OH)$_2$ is formed from 1,4-butanediol, 2,2-dimethyl1,3-propanediol, 1,2-cyclohexanediol, 1,3-cyclohexanediol or 1,4-cyclohexanediol.

8. A process according to claim 1 where, when b is 3,
—E—(OH)$_3$ is a carbon centered radical formed from 1,1,1-tris(hydroxymethyl)ethane, 2-ethyl2-(hydroxymethyl)-1,3-propanediol, 1,2,4-butanetriol or 1,2,6-hexanetriol.

9. A process according to claim 8 wherein —E—(OH)$_3$ is formed from 1,1,1-tris(hydroxymethyl)ethane or 2-ethyl2-(hydroxymethyl)-1,3-propanediol.

10. A process according to claim 1 wherein b is 1 or 2.

11. A process according to claim 10 wherein b is 1.

12. A process according to claim 1 wherein the peroxide is hydrogen peroxide, the addition compound of urea and hydrogen peroxide, tert-butyl hydroperoxide, tert-amyl hydroperoxide or cumene hydroperoxide.

13. A process according to claim 12 wherein the peroxide is hydrogen peroxide or the addition compound of urea and hydrogen peroxide.

14. A process according to claim 13 wherein the peroxide is hydrogen peroxide.

15. A process according to claim 1 wherein the metal is chosen from the group IVA, VA, VIIA, VIIIA and IB of the periodic table.

16. A process according to claim 15 wherein the metal is iron(II), iron(III), copper(I), copper(II), cobalt(II), cobalt (III), manganese(II), manganese(III), vanadium(II), vanadium(III), cerium(III) or titanium(III).

17. A process according to claim 16 wherein the metal is iron(II), iron(III), copper(I) or copper(II).

18. A process according to claim 1 wherein the counterion for the above metals is chloride, sulfate, acetylacetonate (acac), acetate, citrate, oxalate, nitrate, perchlorate, cyanide, hydroxide, phosphate, pyrophosphate or oxide.

19. A process according to claim 1 wherein the ligand for the above metals is 2,2'dipyridyl, 2,2':6,2"-terpyridyl, 1,10-phenanthroline, ethylenediaminetetraacetic acid, ethylenediaminetetraacetic acid disodium salt, pyridine, picolinic acid, 2-pyrazinecarboxylic acid, aromatic diimines formed from the reaction of aniline or substituted anilines with 1,2-diketones such as 2,3-butanedione, or triphenylphosphine oxide.

20. A process according to claim 1 wherein the metal salt is ferrous chloride, ferric chloride, ferric acetylacetonate, ferric phosphate, ferric pyrophosphate, ferrous phosphate, ferrous sulfate, ferric sulfate, ferrous acetate, ferric citrate, ferrous oxalate, ferric oxalate, ferric nitrate, ferrous perchlorate, ferric perchlorate, cuprous chloride, cupric chloride, cuprous sulfate, manganous chloride, sodium metavanadate, titanous chloride, vandium(II) chloride or vanadium(III) chloride.

21. A process according to claim 20 wherein the metal salt is ferrous chloride, ferric chloride, ferric acetylacetonate, ferric phosphate, ferric pyrophosphate, ferrous phosphate, ferrous sulfate, ferric sulfate or cupric sulfate.

22. A process according to claim 1 wherein the metal-ligand complex is from iron(II), iron(HI), copper(I) or copper(II) salts and 2,2'-dipyridyl, triphenylphosphine oxide, ethylenediaminetetraacetic acid or ethylenediaminetetraacetic acid disodium salt.

23. A process according to claim 22 wherein the metal-ligand complex is from ferrous chloride or ferric chloride and 2,2'-dipyridyl.

24. A process according to claim 1 wherein an acid which is hydrochloric acid, sulfuric acid, methanesulfonic acid, oxalic acid, trifluoroacetic acid, polyphosphoric acid or phosphoric acid.

25. A process according to claim 24 wherein the acid is polyphosphoric acid or phosphoric acid.

26. A process according to claim 24 wherein the acid is methanesulfonic acid.

27. A process according to claim 1 wherein the ratio of 5 to 100 moles of solvent per mole of nitroxyl moiety is used.

28. A process according to claim 27 wherein the ratio is 10 to 50 moles of solvent per mole of nitroxyl moiety is used.

29. A process according to claim 28 wherein the ratio is 10 to 30 moles of solvent per mole of nitroxyl moiety.

30. A process according to claim 1 wherein the amount of hydrogen peroxide or organic hydroperoxide is 1 to 20 moles per mole of nitroxyl moiety.

31. A process according to claim 30 wherein the amount is 1 to 5 moles of peroxide or hydroperoxide per mole of nitroxyl moiety.

32. A process according to claim 31 wherein the amount is 1 to 3 moles of peroxide or hydroperoxide per mole nitroxyl moiety.

33. A process according to claim 1 wherein the amount of metal salt or metal-ligand complex is 0.001 to 0.5 molar equivalent of metal salt or metal-ligand complex per mole of nitroxyl moiety.

34. A process according to claim 33 wherein the amount of metal salt or metal complex is 0.001 to 0.05 moles of metal salt or metal-ligand complex per mole of nitroxyl moiety.

35. A process according to claim 1 where when an acid is used, the amount of acid is 0.01 to 1 molar equivalent per mole of nitroxyl moiety.

36. A process according to claim 35 wherein the amount of acid is 0.01 to 0.5 molar equivalents of acid per mole of nitroxyl moiety.

37. A process according to claim 1 wherein the process is run at a temperature of 20° to 100° C.

38. A process according to claim 37 wherein the process is run at a temperature of 60° to 100° C.

39. A process according to claim 1 wherein a cosolvent is used.

40. A process according to claim 39 wherein the cosolvent is water, methanol or ethylene glycol.

* * * * *